(12) United States Patent
Lex

(10) Patent No.: US 7,973,932 B2
(45) Date of Patent: Jul. 5, 2011

(54) APPARATUS FOR DETERMINING OPTICAL SURFACE PROPERTIES OF WORKPIECES

(75) Inventor: Konrad Lex, Koenigsdorf (DE)

(73) Assignee: BYK-Gardner GmbH (DE)

( * ) Notice: Subject to any disclaimer, the term of this patent is extended or adjusted under 35 U.S.C. 154(b) by 164 days.

(21) Appl. No.: 12/400,610

(22) Filed: Mar. 9, 2009

(65) Prior Publication Data
US 2009/0225318 A1    Sep. 10, 2009

(30) Foreign Application Priority Data

Mar. 10, 2008 (DE) .................. 10 2008 013 387

(51) Int. Cl.
- G01J 3/46 (2006.01)
- G01N 21/55 (2006.01)
- G01N 21/88 (2006.01)
- G01B 11/24 (2006.01)

(52) U.S. Cl. ........ 356/402; 356/601; 356/445; 356/446; 356/237.2

(58) Field of Classification Search .................. 356/402, 356/425
See application file for complete search history.

(56) References Cited

U.S. PATENT DOCUMENTS

| | | | | |
|---|---|---|---|---|
| 3,519,360 A | * | 7/1970 | Kudlek | 356/425 |
| 5,189,490 A | * | 2/1993 | Shetty et al. | 356/600 |
| 5,825,499 A | * | 10/1998 | Biedermann | 356/394 |
| 6,204,923 B1 | * | 3/2001 | Willing | 356/402 |
| 7,468,800 B2 | | 12/2008 | Schwarz et al. | 356/630 |
| 2005/0018191 A1 | * | 1/2005 | Luo et al. | 356/404 |

FOREIGN PATENT DOCUMENTS

DE    10 2005 025 291    12/2006

* cited by examiner

Primary Examiner — F. L Evans
(74) Attorney, Agent, or Firm — Hayes Soloway P.C.

(57) ABSTRACT

The invention relates to an apparatus for determining optical surface properties of workpieces, comprising a housing, in the interior of which there is provided a carrier on which the workpiece be arranged, and comprising a radiation device which directs radiation onto the workpiece in a predefined emission direction (E). According to the invention, the housing has in at least one wall an observation opening, through which a region of the workpiece illuminated by the radiation device can be observed in a predefined observation direction (B).

13 Claims, 2 Drawing Sheets

APPARATUS FOR DETERMINING OPTICAL SURFACE PROPERTIES OF WORKPIECES

Description

The invention relates to an apparatus for determining optical surface properties of workpieces.

A large number of apparatuses for determining surface properties are known from the prior art. For example, DE 10 2005 025 291 A1 discloses a method and an apparatus for determining surface properties. This apparatus is guided over a surface and radiation reflected by the surface is evaluated by a radiation detector device. Such apparatuses operate in a satisfactory manner. Nevertheless, it is desirable to carry out a direct evaluation of surface properties even of large workpieces, in particular by means of the human eye.

The object of the present invention is therefore to provide an apparatus for determining optical surface properties which allows the user to carry out an evaluation of the surface to be analyzed, in a manner that is as objective as possible. This is achieved according to the invention by an apparatus according to claim 1. Advantageous embodiments and further developments form the subject matter of the dependent claims.

An apparatus according to the invention for determining optical surface properties of workpieces comprises a housing, in the interior of which there is provided a carrier on which a workpiece to be analyzed can be arranged. The apparatus also comprises a radiation device which directs radiation onto the workpiece in a predefined emission direction. According to the invention, the housing has in at least one wall an observation opening, through which a region of the workpiece illuminated by the radiation device can be observed in a predefined observation direction.

A workpiece is understood to mean in principle any workpieces having surfaces which are to be optically evaluated. Preferably, however, these workpieces are in particular parts of motor vehicles, such as for example doors, wings, side parts, but also sample sheets and the like. Optical surface properties are understood to mean for example gloss, orange peel, color, macrostructure or microstructure, image sharpness, haze, cloudiness, surface structure and/or surface topography. In addition, the optical surface properties may also be the properties of so-called effect pigments or sparkles, which may differ considerably depending on the observation angle. Providing an observation opening means that an observer always observes the workpiece under precisely defined preset conditions, in particular at a predefined observation angle relative to the interior of the housing.

The apparatus according to the invention therefore makes it possible to check the correct function of other devices for analyzing surface properties. Such other devices may be for example standardized gloss and color measuring devices, which are specified for example in ASTM, DIN or ISO. In these specifications, the angles and apertures for illumination and observation are described in particular for these measuring devices. Preferably, therefore, specified illuminations (angles and/or apertures) are carried out. Preferably, standardized types of light such as A, C or D65 are also used for the type of illumination.

Preferably a pivoting device is provided, by means of which the carrier can be pivoted about a predefined pivot axis. It is thus possible to pivot the carrier and the workpiece arranged on this carrier relative to the housing, and thus also to vary the angle at which the workpiece is observed by the observer. It is pointed out that, in this embodiment, the actual observation direction relative to the housing still remains constant, but the position or pivot position of the workpiece relative to the housing itself changes. In the simplest case, the pivoting device is a shaft, on which the carrier is arranged.

In a further advantageous embodiment, a coupling device is provided, by means of which the radiation device is coupled to the carrier. This means that here, in the event of a pivoting movement of the carrier and thus also of the workpiece, the radiation device is also pivoted. In this embodiment, therefore, the angle at which the radiation device emits radiation and in particular light onto the workpiece remains constant. Conversely, it would also be conceivable to arrange the carrier in a fixed position and to provide a possibility for changing the emission angle of the radiation device. For example, a guide rail for the radiation device could be provided, by means of which the radiation device can be pivoted relative to the workpiece or about the workpiece.

Preferably, an actuating device for changing the pivot position of the carrier is provided outside the housing. It would thus be possible to provide on an outer wall of the housing for example an actuating lever which can be pivoted, wherein the carrier and thus also the workpiece are pivoted at the same time with this actuating lever. However, it would also be possible to provide a motor control system here, by means of which a user can input for example from outside certain angle presets which are then set automatically. Finally, it would also be possible to pivot the housing itself or to provide the observation opening in such a way that the workpiece can be observed at different angles. However, the apparatus shown here has the advantage that the user can always assume a precisely defined position relative to the apparatus.

In a further advantageous embodiment, the pivot axis is essentially perpendicular to a plane which is formed by the emission direction and the observation direction. This will be explained in more detail with reference to the figures.

In a further advantageous embodiment, the housing is essentially closed. Essentially closed is understood to mean that the housing is closed in particular apart from the observation opening. This prevents light from impinging on the workpiece from outside and falsifying the observation. In a further advantageous embodiment, the observation device comprises a slot arranged in a housing wall, wherein this slot extends parallel to the pivot axis of the carrier. In this embodiment, it is possible to observe the workpiece along the entire longitudinal direction of the pivot axis, in particular when an illumination of the workpiece likewise takes place along the entire pivot axis.

In a further advantageous embodiment, the radiation device is arranged in the interior of the housing. It would thus be possible for example to provide fluorescent tubes in the interior of this housing. However, it would also be conceivable to arrange a radiation source outside the housing and to guide the light thereof into the interior of the housing, for example by means of fiber optic cables and the like.

In a further advantageous embodiment, the inner walls of the housing are made of a light-absorbing material. It would thus be possible for example to equip the inner walls with photoresist or with felt, which absorb light. In this way, it is possible to render an optical impression of the workpiece which is not falsified by other influences. However, it would also be possible to configure the inner surface of the housing to be diffusely reflective, for example matt. In this way, it would be possible to simulate an illumination of the workpiece from all sides or an illumination when the sky is cloudy.

In a further advantageous embodiment, the radiation device comprises a spot-type light source. It would be possible to provide a plurality of spot-type light sources along the pivot axis of the carrier. However, it would also be possible to provide a tube light, in particular a D65 tube light, which extends parallel to the pivot axis of the carrier. Between this fluorescent tube or in general the light source and the carrier, diaphragm devices could be provided which generate the emission characteristic of a spot-type light source or of a defined aperture. A plurality of radiation devices could also be provided which emit light with different special components or different colors, in order in this way to mix white light or the abovementioned standardized types of light.

In a further advantageous embodiment, the apparatus comprises a display device which displays a pivot position of the carrier. It is thus possible to read, in particular by means of a display device arranged externally on the housing, such as a scale, the current pivot position of the carrier device and thus also of the workpiece relative to the observation direction.

In a further advantageous embodiment, the apparatus comprises a plurality of radiation devices. It is thus possible to illuminate the workpiece at fixedly predefined angles and accordingly to observe this illuminated surface. In this case, the movements of this radiation device is preferably also coupled to the carrier device, that is to say they are also pivoted when the carrier is pivoted. Preferably, this plurality of radiation devices can be switched on and off separately, so that it is possible to simulate impinging light at different angles. In a further advantageous embodiment, at least one radiation device can be adjusted with regard to its brightness. The workpiece is thus illuminated at constant angles and observed at varying angles. In a further embodiment, a radiation device illuminates the workpiece indirectly.

Advantageously, a support element for the workpiece is provided on the carrier, wherein this support element is movable relative to the carrier. In this case, it is also possible to observe workpieces of greater or different thickness. More specifically, this support element can be moved in such a way that the surface of the workpiece itself coincides with the pivot axis.

In a further advantageous embodiment, the apparatus comprises a vision guiding device which defines the viewing direction towards the workpiece. This may be for example an ocular or a tube, through which the vision is directed onto the pivot axis or the surface section provided on the pivot axis. In this way, the viewing direction of the observer is defined more precisely. In this case, it would be possible to attach an objective to the outside of the housing, by means of which a precisely defined region of the workpiece can be observed.

In a further advantageous embodiment, provided outside the housing is a darkening device which prevents light from entering the interior of the housing through the observation opening. As mentioned above, preferably the housing is completely closed, so that no light can enter inwards from outside. This darkening device thus prevents light from entering the interior of the housing through the necessary observation opening and falsifying the observation.

Preferably, this darkening device may be a labyrinth or a curtain, wherein the observer can step for example between a side wall and this curtain so that an illumination from outside is prevented.

In a further advantageous embodiment, the pivoting device has at least one predefined locked position. Certain illumination and observation angles are uniformly standardized, so that it is advantageously possible to set the carrier and thus also the workpiece at these predefined observation angles, for example an angle of 15° with an illumination angle of 45°.

Preferably, angles according to the customary color standards can be set, and particularly preferably the angles 15°, 25°, 45°, 75°, 110° in relation to the reflection angle. With particular preference, it is also possible to set angles which lie on the opposite side of the reflection axis, such as for example the angle −15° or also the respective negative angles to the abovementioned positive angles.

During the observation, instead of or in addition to the observation at 45° described here, an observation at a different angle could also be set. To this end, it would be possible both to displace the observation opening and to rotate the sample.

Preferably, the apparatus in its entirety is height-adjustable, for example by using a scissors-lift table arranged below the apparatus.

In a further advantageous embodiment, the apparatus comprises an image recording device which observes an illuminated region of the workpiece. This may be for example a camera which is arranged in the interior of the housing and which additionally records the surface. Besides the evaluation by means of the human eye, the optical impression can thus additionally be recorded electronically.

Further advantages and embodiments will emerge from the appended drawings:

Figure 1:
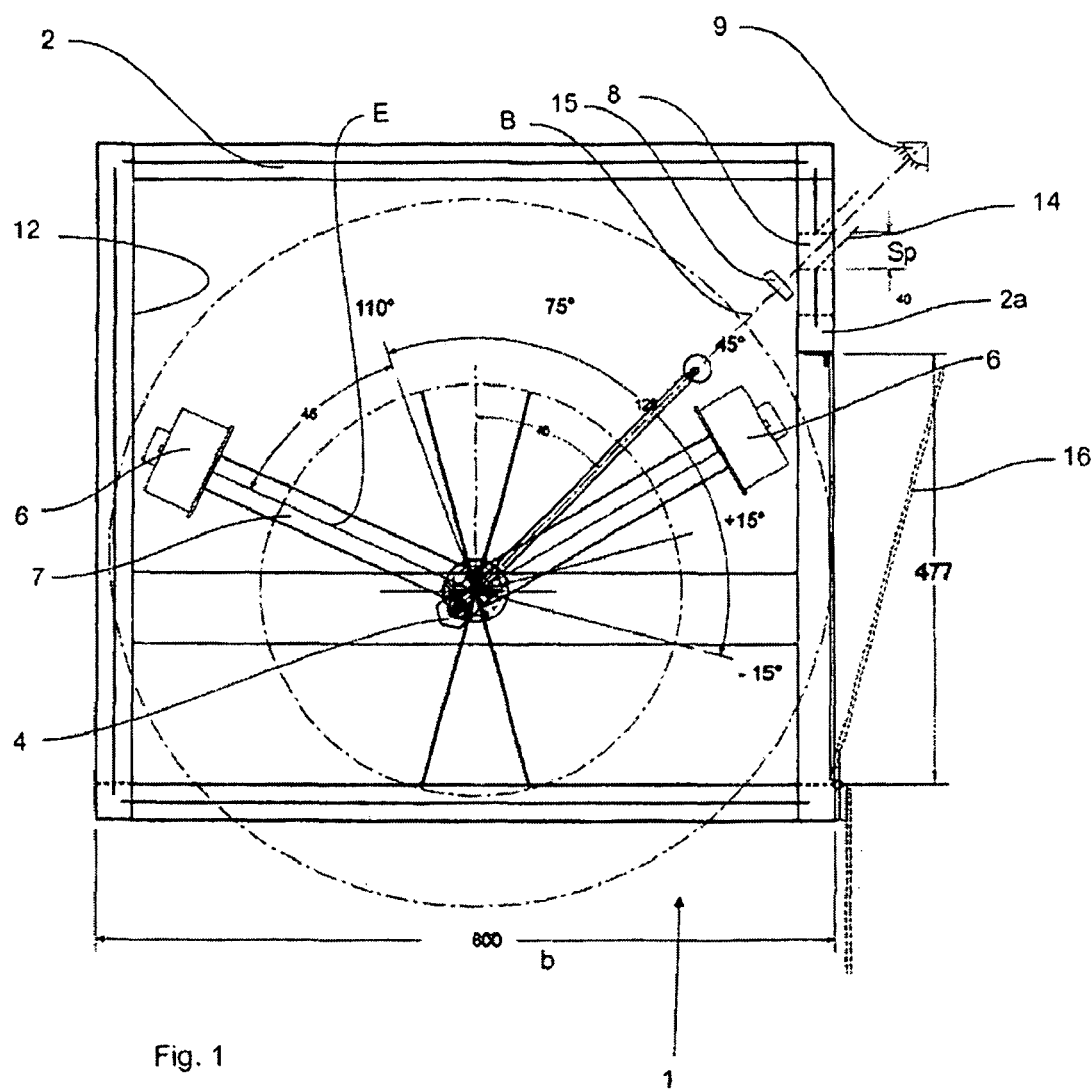
FIG. 1 shows a section through an apparatus according to the invention.

FIG. 1 shows an apparatus 1 according to the invention. This apparatus 1 comprises a housing 2 which is closed on all sides. Provided within the housing 2 is a carrier 4 which can be pivoted about a pivot axis, this pivot axis being perpendicular to the plane of the figure. Fixing means for fixing the workpiece may be provided on this carrier in order to prevent the workpiece from sliding off the carrier device in certain pivot positions. The carrier is advantageously configured in such a way that even heavy workpieces can be carried by it and pivoted.

Reference 6 denotes a radiation device which emits light in the direction of the carrier device and thus also in the direction of a workpiece arranged on the carrier device 4. This radiation device is coupled to the carrier by means of a coupling device 7, which may be for example a rod or the like, and is thus pivoted along with the carrier when the latter is pivoted by the corresponding angle. The radiation device 6 thus emits light onto the carrier in the emission direction E. This emission direction E relative to the carrier and also the observation aperture are constant as a result of the coupling.

On the right-hand side in FIG. 1, a further radiation device 6 is provided which is likewise coupled to the pivoting movement of the carrier 4.

Reference 8 denotes an observation opening which is provided in a side wall 2a of the housing 2. Through this observation opening 8, an observer 9 can see into the interior of the housing 2, the observation direction B being precisely fixed. In this case, it is possible to provide a vision guiding device 14 which causes the observation direction to be set in a very precise manner. It is pointed out that it is not the observation direction relative to the workpiece itself that is set, since the latter can be pivoted, but rather the observation direction relative to the housing or in this case also relative to the pivot axis of the carrier.

A diaphragm 15 may be provided between this observation opening 8 and the sample 10 in order to set different apertures. This diaphragm may be movable. Such optionally movable diaphragms for setting or simulating different apertures may also be present between the illumination device and the sample (10). However, it is also possible that the observation opening itself acts as the diaphragm.

Reference 16 denotes an opening flap, via which the housing can be opened and in this way the workpiece can be removed from the housing. By opening this flap 16, an opening of the housing is therefore exposed which preferably has a height h of at least 350 mm, preferably of at least 400 mm and particularly preferably of at least 450 mm. The housing 2 itself has a width b of more than 500 mm, preferably more than 600 mm and particularly preferably more than 700 mm.

By contrast, the gap width Sp of the observation opening is less than 100 mm, preferably less than 80 mm and particularly preferably less than 50 mm. The pivoting range within which the carrier can be pivoted is more than 20°, preferably more than 40°, preferably more than 60° and particularly preferably more than 120°.

Reference 12 denotes an inner wall of the housing 2. This inner wall is designed here to be absorbent. In a further embodiment, the housing has guides in its interior so as to be able to introduce differently configured walls, for example white or reflective walls. In this case, guides such as slots may be provided for example on all the inner walls or in the corners of the housing, into which additional walls are pushed for example from above or also from below, (i.e.) through the bottom. Corresponding guides could also be provided on the bottom and top faces of the housing. The housing could also have a frame into which optionally different side walls and also top and bottom faces can be pushed. Finally, it would also be possible to equip the individual walls of the housing with different surfaces, for example an absorbent surface on one side and a reflective surface on the other side. In this way, the interior could be reconfigured from absorbent to reflective by turning over the individual walls.

Figure 2:
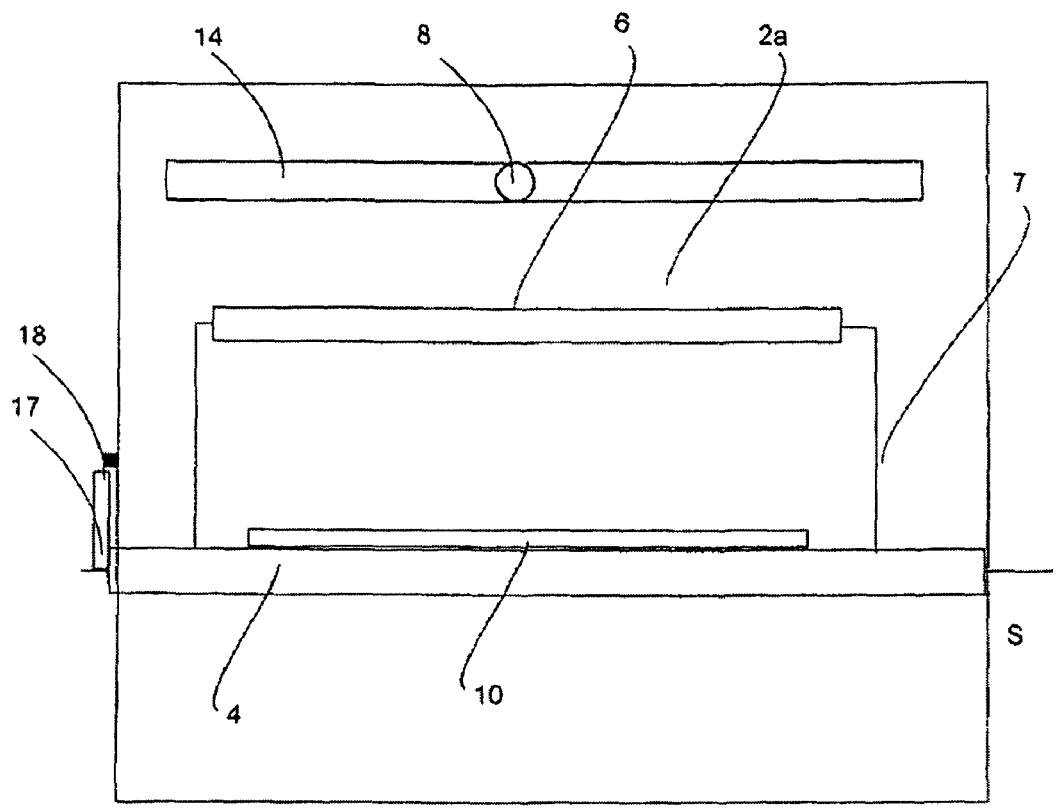
FIG. 2 shows a schematic side view of the opened apparatus from FIG. 1.

FIG. 2 shows a side view of the apparatus shown in FIG. 1 for determining optical surface properties. It can be seen here that a workpiece 10 is arranged on the carrier 4. At the same time, there is also provided an actuating element 17 in the form of a lever which is arranged outside the housing and by means of which the carrier 4 can be pivoted about the pivot axis S. Reference 18 denotes a display device such as a scale, on which the corresponding pivot angle can be read.

Here too, reference 7 again denotes the coupling device (shown only schematically), by means of which the radiation device 6 is coupled to the pivoting movement of the carrier 4. The radiation device 6 is designed here as a tube light which extends parallel to the pivot axis S. The observation opening 8 is arranged here in an elongate slot 14. Preferably, the observation opening is displaceable relative to this slot 14, in order in this way to be able to observe the workpiece 10 along its entire longitudinal extent. In this case, elements would be conceivable which cause the slot 14 to be darkened, apart from the region in which the observation device is provided. For instance, a backdrop or a curtain could be provided which preferably completely darkens this slot 14 in order to prevent light from impinging through this slot 14 into the interior of the housing 2.

Figure 3:
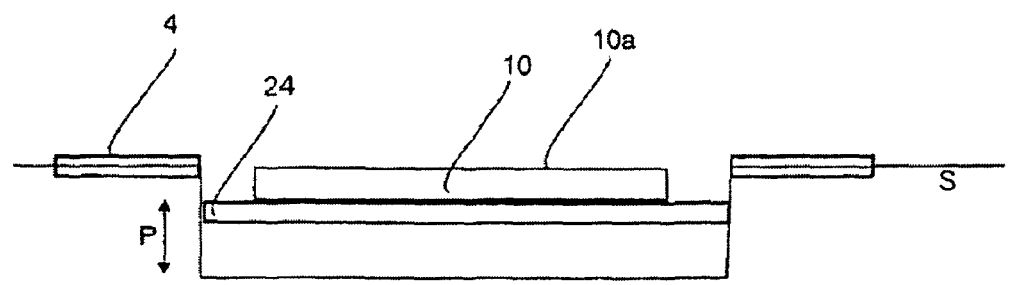
FIG. 3 shows one preferred embodiment of a carrier with a support element.

FIG. 3 shows a further embodiment of a carrier 4 according to the invention. It can be seen here that a support element 24 is provided on the carrier, which support element is displaceable in its height position, that is to say along the double arrow P. In this way, a workpiece 10 can always be arranged in such a way that its surface 10a coincides at least partially with the pivot axis S. In this way, as a result of a pivoting movement of the carrier, the surface 10a is precisely pivoted in order in this way to allow a precise observation of this surface. A displacement of the support element 24 relative to the carrier is possible for example by means of screw connections, by means of clamping connections or the like. Furthermore, it would also be possible to permit different heights of the support element at both sides, in order in this way to be able to better observe workpieces of varying height.

All of the features disclosed in the application documents are claimed as essential to the invention in so far as they are novel individually or in combination with respect to the prior art.

LIST OF REFERENCES 1 apparatus
2 housing
2a side wall
4 carrier
6 radiation device
7 coupling device
8 observation opening
9 observer
10 workpiece
10a surface
12 inner wall of the housing 2
14 slot
15 diaphragm
16 opening flap
17 actuating element
18 display element
24 support element
b width of the housing
B observation direction
E emission direction
P double arrow, displacement direction
S pivot axis
Sp gap width
b width of the housing 2
h partial height of the housing 2

The invention claimed is:

1. An apparatus for determining optical surface properties of workpieces, comprising an essentially closed housing, in the interior of which there is provided a carrier on which the workpiece can be arranged, and comprising a radiation device which directs radiation onto the workpiece in a predefined emission direction (E), wherein the radiation device is coupled to the carrier by a coupling device, and wherein the housing has in at least one wall an observation opening, through which a region of the workpiece illuminated by the radiation device can be observed in a predefined observation direction (B), and comprising a vision guiding device for defining the predefined observation direction (B) in a direction towards the workpiece.

2. The apparatus according to claim 1, wherein a pivoting device is provided, for pivoting the carrier about a predefined pivot axis (X).

3. The apparatus according to claim 2, wherein at least one actuating device for changing the pivot position of the carrier is provided outside the housing.

4. The apparatus according to claim 2, wherein the pivot axis is essentially perpendicular to a plane which is formed by the emission direction (E) and the observation direction (B).

5. The apparatus according to claim 1, wherein the observation device is a slot arranged in a housing wall, which slot extends parallel to a pivot axis of the carrier.

6. The apparatus according to claim 1, wherein the radiation device is arranged in the interior of the housing.

7. The apparatus according to claim 1, wherein inner walls of the housing are made of a light-absorbing material.

8. The apparatus according to claim 1, wherein the apparatus comprises a display device which displays a pivot position of the carrier.

9. The apparatus according to claim 1, wherein the apparatus comprises a plurality of radiation devices.

10. The apparatus according to claim 1, wherein a support element for the workpiece is provided on the carrier, wherein this support element is movable relative to the carrier.

11. The apparatus according to claim 1, wherein provided outside the housing is a darkening device which prevents light from entering the interior of the housing through the observation opening.

12. The apparatus according to claim 2, wherein the pivoting device has at least one predefined locked position.

13. The apparatus according to claim 1, wherein at least one radiation source comprises a spot-type light source.

* * * * *